(12) United States Patent
Griebel

(10) Patent No.: US 8,454,825 B2
(45) Date of Patent: Jun. 4, 2013

(54) ROD ASSEMBLY AND A METHOD FOR THE EXTRACTION OF MAGNETIZABLE PARTICLES FROM SOLUTIONS

(75) Inventor: Ralf Griebel, Birkenfeld (DE)

(73) Assignee: Stratec Biomedical AG, Birkenfeld (DE)

(*) Notice: Subject to any disclaimer, the term of this patent is extended or adjusted under 35 U.S.C. 154(b) by 271 days.

(21) Appl. No.: 12/778,219

(22) Filed: May 12, 2010

(65) Prior Publication Data

US 2010/0288705 A1 Nov. 18, 2010

(30) Foreign Application Priority Data

May 13, 2009 (DE) .......................... 10 2009 021 201

(51) Int. Cl.
*B03C 1/28* (2006.01)
(52) U.S. Cl.
USPC ............ 210/222; 436/526; 422/50; 422/68.1; 422/561
(58) Field of Classification Search
USPC ..................... 210/222; 436/526; 422/50, 68.1, 422/561
See application file for complete search history.

(56) References Cited

U.S. PATENT DOCUMENTS

| | | | |
|---|---|---|---|
| 5,647,994 A | 7/1997 | Tuunanen et al. | |
| 5,837,144 A | 11/1998 | Bienhaus et al. | |
| 6,033,574 A | 3/2000 | Siddiqi | |
| 6,207,463 B1 | 3/2001 | Tuunanen | |
| 6,409,925 B1 | 6/2002 | Gombinsky et al. | |
| 7,347,338 B2 | 3/2008 | Korpela | |
| 2001/0022948 A1 | 9/2001 | Tuunanen | |
| 2006/0266130 A1 | 11/2006 | Zobel et al. | |

FOREIGN PATENT DOCUMENTS

| | | |
|---|---|---|
| DE | 4421058 A1 | 12/1995 |
| EP | 0687505 A1 | 12/1995 |
| EP | 1058851 B1 | 7/2005 |
| EP | 1726963 A2 | 11/2006 |
| WO | 8606493 A1 | 11/1986 |
| WO | 8705536 A1 | 9/1987 |
| WO | 9612958 A1 | 5/1996 |
| WO | 0168263 A1 | 9/2001 |
| WO | 02066165 A2 | 8/2002 |
| WO | 2004035217 A1 | 4/2004 |
| WO | 2008045742 A1 | 4/2008 |
| WO | 2008131554 A1 | 11/2008 |

*Primary Examiner* — David A Reifsnyder
(74) *Attorney, Agent, or Firm* — Hultquist, PLLC; Steven J. Hultquist; Mary B. Grant

(57) ABSTRACT

A rod assembly for the extraction of magnetizable particles from solutions is described. The rod assembly includes at least one guide element. A rod element is insertable into the at least one guide element and moveable in a direction substantially parallel to the at least one guide element. A magnet element is moveable to a distal magnet element position; wherein the distal magnet element position is located on a distal end section of the at least one guide element; wherein the at least one guide element includes an opening at a distal end. A method for the extraction of magnetizable particles from solutions is also described, as well as a magnet element for the extraction of magnetizable particles from solutions.

42 Claims, 11 Drawing Sheets

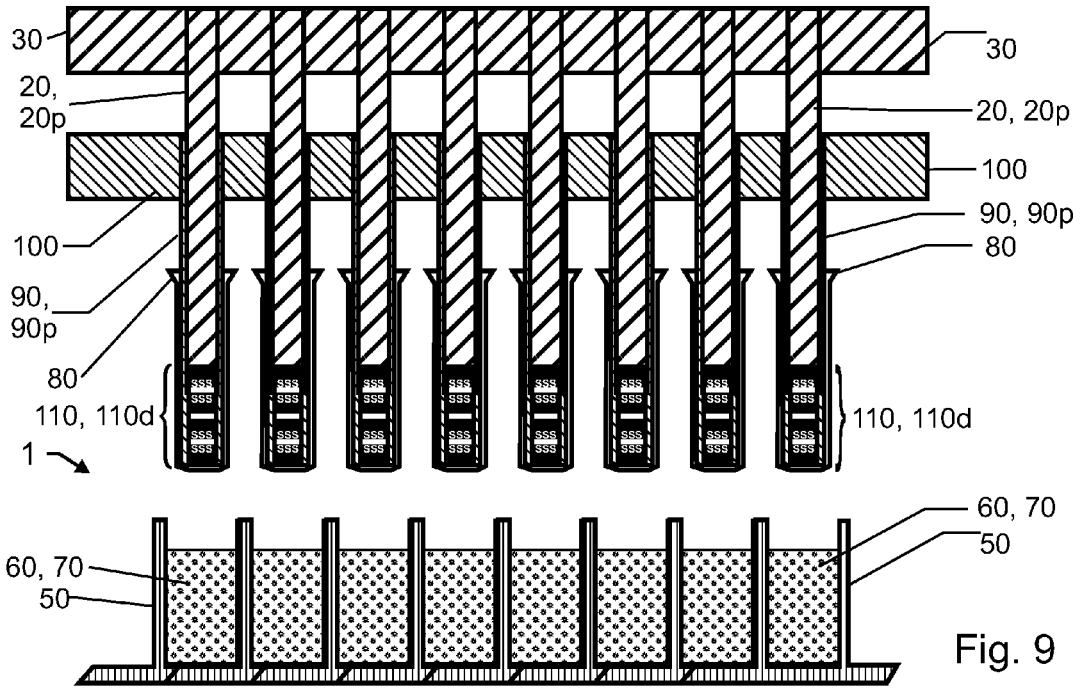
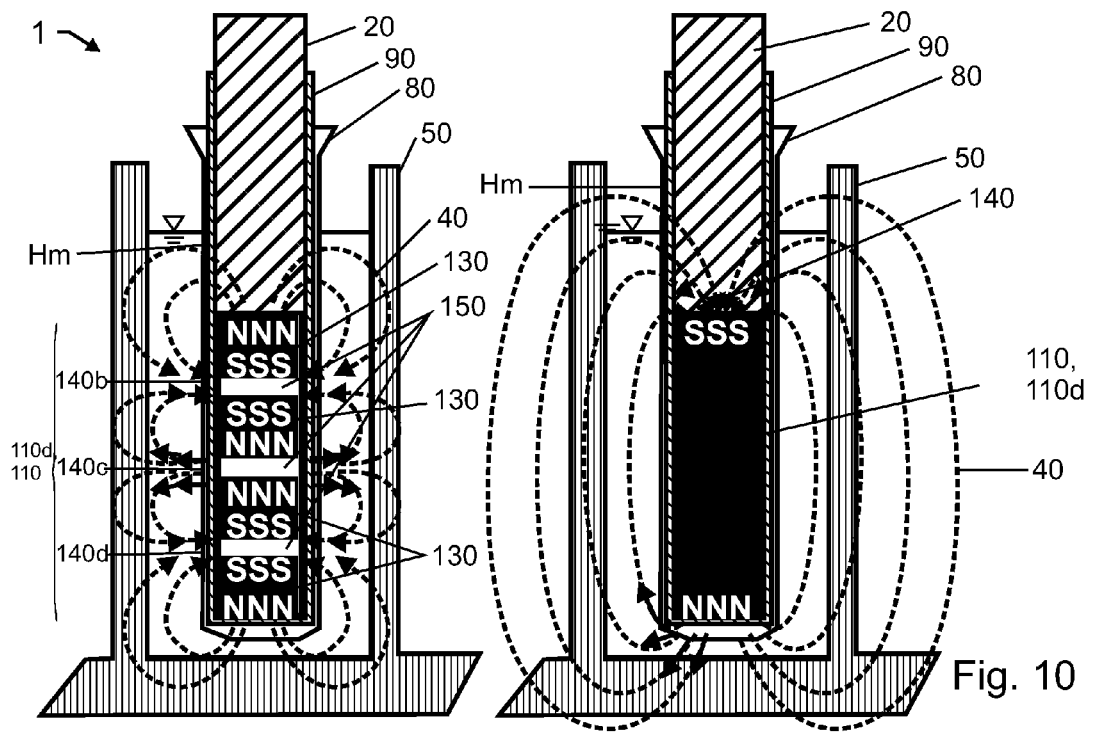
Fig. 9
Fig. 10

ROD ASSEMBLY AND A METHOD FOR THE EXTRACTION OF MAGNETIZABLE PARTICLES FROM SOLUTIONS

CROSS REFERENCE TO RELATED APPLICATION

The present application claims the benefit and priority of German Patent Application No. 10 2009 021 201.9 filed on 13 May 2009. The disclosure of German Patent Application No. 10 2009 021 201.9 is hereby incorporated herein by reference in its entirety, for all purposes.

DESCRIPTION

1. Field of Invention

The field of the present invention relates to the extraction of magnetizable particles from a solution in at least one cavity. Furthermore the field of the present invention relates to a method for the extraction of magnetizable particles from a solution in at least one cavity. Furthermore the field of the present invention relates to magnetic elements for the extraction of magnetizable particles.

2. Background of Invention

In the prior art, a rod assembly is known for the extraction of bio-molecules by means of magnetizable particles. The magnetizable particles are initially in a solution in a cavity. Under suitable conditions the biomolecules bind to the magnetizable particles. The suitable conditions include the addition of a binding buffer and possibly a lysis of the biomolecules, as known in the art.

The magnetizable particles are bound to the bio-molecules. By means of a magnetic element of the rod assembly the magnetizable particles and with them the bound biomolecules can be attracted to the rod assembly. Usually repeated cleaning steps are required for the extraction of the magnetizable particles. Purity of the magnetizable particles at the rod assembly is increased with each of the cleaning steps. Typically the magnetizable particles with the bio-molecules attached thereto are transferred by means of the rod assembly from one cavity to a further cavity.

Simple magnetizable rod assemblies are known in the art. The rod assembly is used, for example, in devices for laboratory automation, in order to transport magnetizable particles. A rod in the prior art is often coated with a sheath with a sealed base which is open at the top. The rod is then contacted with the solution of magnetizable particles. A magnetic element at the inside is moved to an area at the lower end, i.e. a distal end of the rod. The magnetic attraction enables transport of the magnetizable particle possible from the solution and into further cavities. In order to deposit the magnetizable particles in the further cavity, the magnetic element is switched off. Switching off the magnetic element can be achieved by removal of the magnetic element from the sheath. Alternatively switching off current to the magnetic element is possible, if the magnetic element is implemented as an electromagnet.

WO 198705536 (Carbo Matrix, 1986) describes a method for manipulating magnetic particles using magnetizable elements. It uses a plastic sheath of the magnetic rod. The plastic sheath is substantially non-magnetic. The plastic sheath comprises usually a thin-walled, non-magnetizable and a magnetic reminance-free material. The Carbo Matrix system further describes a movement of the magnetic element within the non-magnetic sheath. A distal end of the plastic sheath has a stepped profile. The stepped profile ensures that the magnetizable particles basically deposit themselves at that top and not at a side of the plastic sheath.

U.S. 20060266130 (Festo, 2005) describes an automated processing device with magnetizable rods and magnetizable particles. This patent application gives a comprehensive overview of the development of so-called "magnetic bead" technologies. In the case of magnetic beads of the first generation, magnets were attached to the bottom to attract the magnetizable particles downwards. Then followed various configurations with the magnetizable rods inserted from the top into cavities. The Festo 2005 system is targeted at relatively large magnetizable particles that reach high speeds within a solution. Furthermore the Festo 2005 system provides only a small magnetically effective surface. By the term "a magnetically effective surface a surface," of a casing is to be understood, which is inter-dispersed with a sufficiently strong and inhomogeneous magnetic field, in order to deposit the magnetizable particles. The magnetically effective surface is determined by a dimension of area sufficiently strongly inter-dispersed by a an inhomogeneous magnetic field and substantially section areas of said area inter-dispersed inhomogeneous magnetic field with the sheath or the walls of the cavities. The Festo 2005 system is unsuitable for use with tiny magnetizable particles.

It is well known in the prior art that magnetizable particles have a diameter of a few micrometers to several ten micrometers. It should be understood that reference to the small magnetizable particles below, means magnetizable particles with a diameter of less than one micron, for example in the range of 100 to 500 nm. The magnetic particles with a diameter smaller than one micron are referred to as "Nanobeads".

WO 8606493 (Labsystems, 1986) describes a method for carrying out immunoassays using magnetizable particles and magnetizable rods. The Labsystems system of 1986 allows a measuring of radiation of magnetizable particles that adhere to the magnetizable rods. The magnetizable rods carry a magnetic element at its tip. The magnetic element at the tip is a short bar magnet. This means that the length of the magnets is comparable to or less than a diameter of the bar magnet. An effective magnetic surface for extraction of magnetizable particles in the Labsystems system of 1986 is limited to the distal end of the rod.

EP 0787296 (Thermo, 1994) describes a magnetizable rod of ferromagnetic material. The magnetizable rod has at a distal end a long bar magnet whose length is at least twice as large as the diameter of the long bar magnet. A ferromagnetic shaft of the magnetizable rod concentrates the magnetic field lines of the magnetic element in the ferromagnetic material, so that the magnetic field lines are brought out of a cavity proximal to the distal end of the magnetizable rod. In the Thermo system of 1994 the effective magnetic field is limited at the distal end of the magnetizable rod.

EP 0687505 (Roche, 1994) discloses a downwardly open cavity in which a solution is drained down after the magnetizable particles contained therein have been deposited on a chain of alternating magnets. The chain of alternating magnets is protected by a protective cover from the solution.

WO 2002066165 (Dexter Magnetic, 2002) discloses a coating which carries alternating magnetization. The alternating magnetization of the coating is caused by alternating magnetized magnetic elements. The coating can be placed beneath multi-well plates, so that magnetic field penetrates from beneath the bottom of the multi-well plate. The magnetic field lines are perpendicular to the plane of the multi-well plate. Within the cavities the magnetic field lines extend in the vertical direction. Consequently the magnetic particles are collected at the bottom of the cavities.

EP 1185372 (Thermo, 2001) discloses a magnetizable rod, in conjunction with a vessel for collecting magnetizable particles from a solution or to provide magnetizable particles to a solution. The magnetizable rod includes a tapered end. The magnetizable particles are accumulated at the tapered end. Due to the tapered end of the magnetizable rod, an area of magnetically active surface is limited to the tapered end of the magnetizable rod. Simultaneously, at the tapered end of the rod a magnetic field strength increases, as is known to the person skilled in the art. The collecting of the magnetizable particles in the Thermo system from 2001 is limited to a very small tip area. Also here only a very small surface is present for gathering the magnetizable particles. The thermal system of 2001 discloses a laminar recess of a cavity. From the laminar recess of the cavity, for example, a circular free space results between the tapering end of the magnetizable rod and a base of the cavity. The circular free space is inter-dispersed in an inhomogeneous magnetic field, so that in this circular free space an accumulation of the magnetizable particles is possible.

WO 2008045742 (Promega, 2006) describes a magnetizable rod with a distal magnet element. In the distal magnet element is a further magnet with transverse magnetization. It is characteristic of the system of Promega 2006 that a north-south orientation of the magnetic poles is substantially perpendicular to a longitudinal axis of the magnetizable rod. In the Promega system of 2006 the magnetizable rod is surrounded by a cover, which consists of for example plastic.

WO 2004035217 (BioNobile, 2002) describes a magnetizable rod with a long bar magnet at a distal end of the magnetizable rod. The long bar magnet has a length considerably larger than a width of the long bar magnet. The long bar magnet is surrounded by a ferromagnetic coating. The ferromagnetic coating may be withdrawn proximally. By pulling off the coating, the magnetic field of the tip is released. The ferromagnetic coating concentrates the field lines of the long bar magnet in its interior, so that no more inhomogeneous magnetic field distributions result in a distal end portion of the magnetic rod, as soon as the ferromagnetic cover substantially covers the length of the long bar magnets.

EP 1726963 (Festo, 2006) discloses a transfer unit for transferring a sample from a source vessel to a target vessel. The transfer unit comprises a closed distal guide element and a magnet element. The Festo 2006 system is suitable for the extraction of common magnetizable particles. The magnet element is moveable inside the guide element. The magnet element always remains a distance from a distal end of the guide element. Thus the strength of an inhomogeneous magnetic field in a magnetically effective surface is limited. The Festo 2006 system is limited to a certain extent to use with small magnetizable particles.

SUMMARY OF INVENTION

The present disclosure relates to a rod assembly for the extraction of magnetizable particles from a solution. The rod assembly comprises at least one guide element, at least one rod element and a magnet element. The at least one guide element is moveable to a distal guide element position. The at least one rod element can be inserted into the at least one guide element. The at least one rod element is also moveable in a substantially parallel direction to the at least one guide element. The magnet element is arranged at a distal end portion of the at least one rod element. The magnet element is also movable to a distal magnet element position. The distal magnet element position is located at the distal end portion of the at least one guide element. The at least one guide element has an opening at a distal end.

The disclosure also relates to a method for the extraction of magnetizable particles from solutions in at least one cavity. The method comprises an uptake of sheaths on at least one of the guide elements. The method further includes a collecting of the magnetizable particles using an opening at a distal end of the guide element. The method can include a mixing of the solutions. The uptake of sheaths may include a closure of the opening at the distal end of the guide element with a sealing element. The closure of the opening at the distal end can also replace the uptake of the sheath.

The disclosure also relates to a magnet element for the extraction of magnetic-magnetizable particles. The magnet element comprises a plurality of rod magnets. At least two of the plurality of rod magnets is arranged in a direction substantially parallel to a longitudinal axis of the magnet element with poles that repel each other. The plurality of rod magnets can include at least one short bar magnet. In a short bar magnet, it is to be understood that a length is less than or equal to the diameter. This length to diameter ratio could be, for example, 1.5:4. The magnet element may further include a spacer element. The spacer element is arranged between at least two of each of the plurality of rod magnets. The at least one spacer element may comprise substantially non-magnetic material. The spacer element can also comprise a soft magnetic substance.

In essence, non-magnetic is to be understood as materials, whose electron system causes no appreciable magnetic moment. Substantially non-magnetic materials are therefore not ferromagnetic. Furthermore substantially non-magnetic materials are not paramagnetic. Neither are substantially non-magnetic materials anti-ferromagnetic. If there is only one atomic diamagnetism, which is not superimposed by a magnetic moment of the electron system, the nuclear diamagnetic contributions are to be permitted. Substantially non-magnetic materials include stainless steel or plastic.

The rod assembly may comprise a cylindrical tube as the guide element. A "thin walled cylindrical tube" is a cylindrical tube with a length that is considerably longer than a wall thickness of the thin walled cylindrical tube. For the practical implementation of the disclosure, for example, a length of about 80 mm is suitable for the cylindrical tube. A wall thickness of the thin-walled cylindrical tube can be for example 0.2 mm. In order to increase the available magnetic field strength outside of the guide element, the wall thickness of the cylindrical tube should be chosen to be as thin as possible. For a typical thin-walled cylindrical tube a length to wall thickness ratio is 400:1. Without limitation, other possible length to wall thickness ratios are possible, while the length is significantly greater than the wall thickness. It is of interest with respect to the guide element, that the thin walled cylindrical tube has sufficient inherent stability. The sufficient inherent stability of the guide element is desirable for an uptake of the sheaths.

The rod element of the rod assembly may comprise a rod like element. Furthermore, the rod element, for example a cylindrical tube, may comprise a thin-walled cylindrical tube. In the case of the rod element the thin-walled cylindrical tube also comprises a substantially longer length of the rod element with respect to the wall thickness of the rod element. The rod element can also be implemented in a form of a wire element or a cord, wherein at one end of the cord the magnet element is attached.

Magnetizable particles bound to biomolecules are also known as a particle-biomolecule complex. The term "magnetizable particle" is to be understood as including the particle-biomolecule complex.

For the extraction of magnetizable particles from a solution an inhomogeneous magnetic field is required to enable a force to attract the magnetizable particles. The rod assembly therefore provides an area with an inhomogeneous field line distribution that can be placed in a solution containing the magnetizable particles. By inserting the inhomogeneous field line distribution into the solution, the magnetized particles are forced to move because of the magnetic force effect on the magnetizable particles. This effect can be either a force of attraction of the magnetizable particles, so that the magnetizable particles are deposited on the magnetized rod. Alternatively, the action of the force can be repulsive. In case of repulsion of the magnetizable particles, they are pushed away from the magnetically active surface. In case of repulsion, for example, a concentration of the magnetizable particles in a floor area of the cavity may result.

The rod assembly for the extraction of biomolecules from solutions according to the present disclosure is suited to provide a high as possible effective area to the circumferential surfaces of the guide element.

The rod assembly allows the use of small magnetizable particles. A small diameter of magnetizable particles is in the range of several hundred nanometers. The small magnetizable particles place demands on strength of the inhomogeneous magnetic field. Due to their small size, the small magnetizable particles move very slowly within the solution. Furthermore the small magnetizable particles require a high as possible effective area on which the magnetizable particles can accumulate and thus the biomolecules. Due to the open design of the distal guide element an increase in the inhomogeneous magnetic field in the distal end of the guide element is possible.

Therefore, the rod assembly is better suited for the purification of small magnetizable particles than in the prior art rod assemblies. The improvements over the prior art apply to both common magnetizable particles as well as to small magnetizable particles.

The present disclosure is further described below with reference to the drawings and selected examples.

DESCRIPTION OF FIGURES

FIG. 9 shows a guide element in a proximal guide element position and a magnet element in a distal magnet element position.

FIG. 10 shows a comparison of the magnetic field line distribution for a magnet element in accordance with the present disclosure and a magnet element according to the state of the art.

DETAILED DESCRIPTION OF INVENTION

For a complete understanding of the present disclosure and the advantages thereof, reference is made to the following detailed description taken in conjunction with the accompanying Figures.

It should be appreciated that the various aspects of the present disclosure herein are merely illustrative of specific ways to make and use the technology and do not therefore limit the scope of disclosure when taken into consideration with the appended claims and the following detailed description and the accompanying Figures.

It should be realized that features from one aspect of the disclosure will be apparent to those skilled in the art from a consideration of the specification or practice of the disclosure disclosed herein and these features can be combined with features from other aspects of the disclosure.

Figure 1:
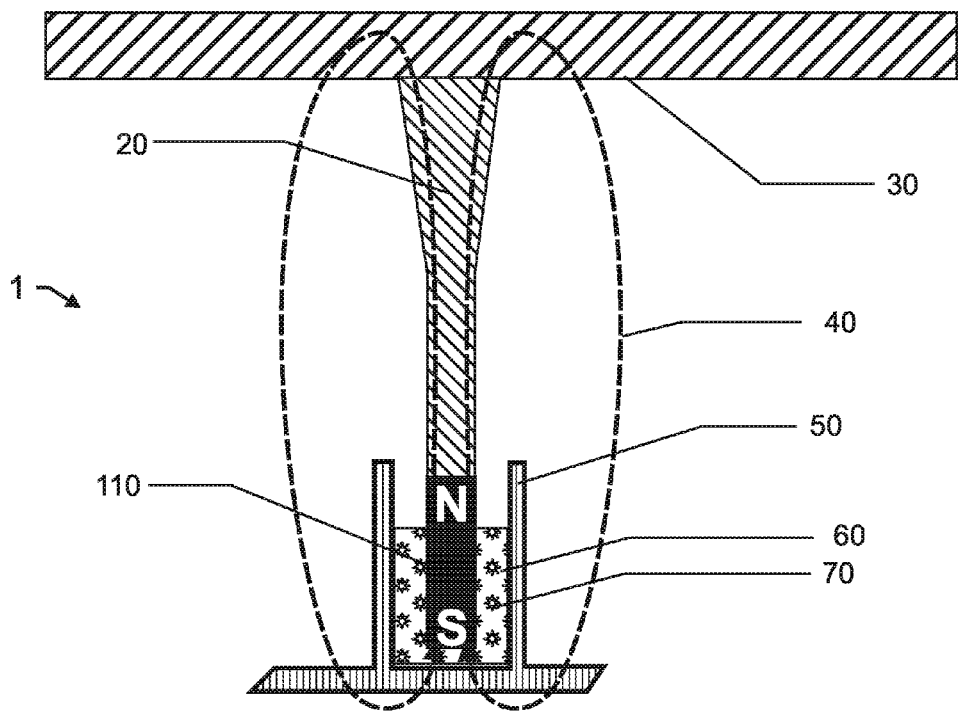
FIG. 1 shows a rod assembly according to the state of the art.

FIG. 1 shows a rod assembly 1. The rod assembly 1 comprises a magnet element 110. In the prior art, the magnet element 110 is in the form of a long permanent magnet or a rod magnet. With a long rod magnet a length of the long rod magnet is larger than a diameter of the rod magnet. The rod magnet can be, for example, of a cylindrical shape. Without limitation other forms of the rod magnet are possible. The length of the magnet element 110 is aligned parallel to a rod element 20. The magnet element 110 is arranged at a distal end section of the rod element 20. The rod element 20 is held by a rod element mechanism. The rod element mechanism can be arranged as a traverse 30 without restriction. A north-south direction of the magnet element 110 in FIG. 1 is arranged parallel to a longitudinal axis of the rod element 20. The north-pole N is at a proximal end, i.e., at the top. The south-pole S is however in FIG. 1 at the bottom or distal end. A reverse orientation would be conceivable for the magnet element 110. In FIG. 1 a magnetic field line distribution 40 of the magnet element 110 is shown. The magnetic field line distribution 40 indicates that at the two poles N and S is an inhomogeneous magnetic field of the magnet element 110. Magnetically effective surfaces substantially result from the magnet element 110 as shown in FIG. 1 and result from the distal end section and a proximal end section of the magnet element 110. For the magnet element 110 in the form of a long rod magnet only the distal end section of the magnet element 110 is available as a magnetically effective surface, since only the distal end section of the magnet element 110 is immersed into a solution 60 with biomolecules 70. The solution 60 is in a cavity 50, into which the magnet element 110 is immersed.

The magnetic field in FIG. 1 and thus the magnetic field line distribution 40 of the magnet element 110 is asymmetrical in a north-south direction. The magnetic field line distribution 40 extends into a proximal range above the magnet element 110. The asymmetrical magnetic field line distribution 40 is caused by the rod element 20 by means of a ferromagnetic material. The ferromagnetic materials concentrate a line of field line distribution in their inside. The ferromagnetic material of the rod element 20 causes an increase in the inhomogeneous magnetic field in the distal end section of the magnet element 110. The increased inhomogeneous magnetic field increases a force on the magnetizable particles 70 in the solution 60, so that the magnetizable particles 70 increasingly deposit themselves at the distal end section of the magnet element 110.

Figure 2:
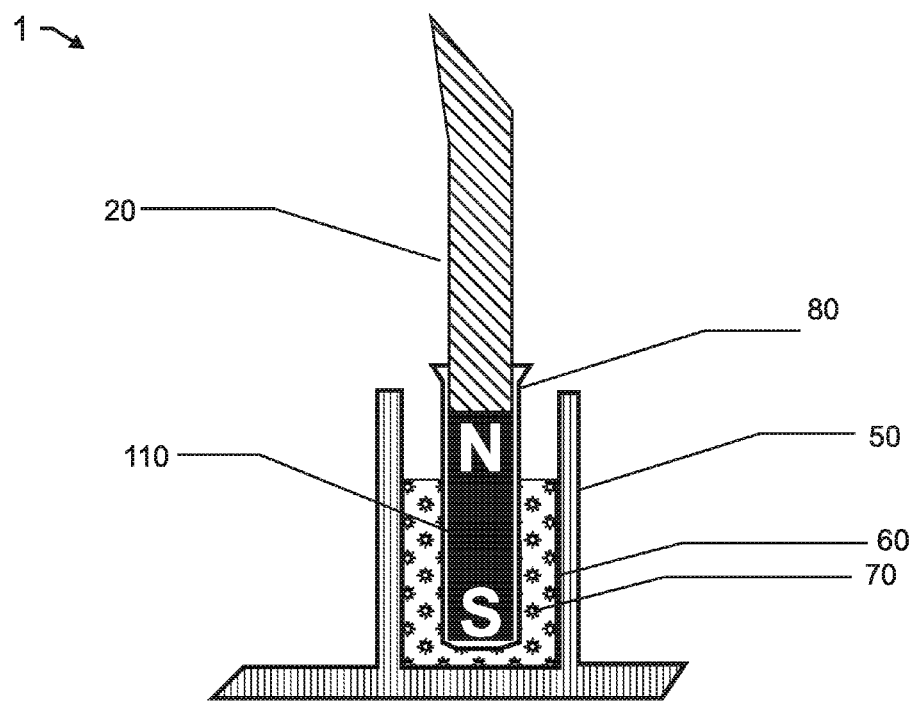
FIG. 2 shows a detail of the rod assembly of FIG. 1 according to the state of the art.

FIG. 2 shows a detail of the rod assembly as shown in FIG. 1. The magnet element 110 and a distal end portion of the rod element 20 are covered with a sheath 80. The sheath 80 consists substantially of a non-magnetic material, e.g. plastic. A wall thickness of the sheath 80 is as thin as possible, in order that the strength of the inhomogeneous magnetic field that interacts with the magnetizable particles 70 in the solution 60 is not weakened any more than necessarily. For the same reason it is favorable to select the sheath 80 from a substantially non-magnetic material. The sheath 80 serves to enable magnetizable particles 70 to settle at exterior surfaces of the sheath 80 and enables the magnetizable particles 70 to separate more easily from the magnet element 110. As the sheath 80 is used, it is sufficient to remove the sheath 80 from the magnet element 110 at the distal end section of the rod element 20 in order to separate the magnetizable particles 70 from the magnet element 110. The use of the sheath 80 therefore avoids the necessary cleaning of the magnet element 110, whereby the cleaning is made more difficult by the attractive reciprocal effect between the magnet element 110 and the magnetizable particles 70.

Figure 3:
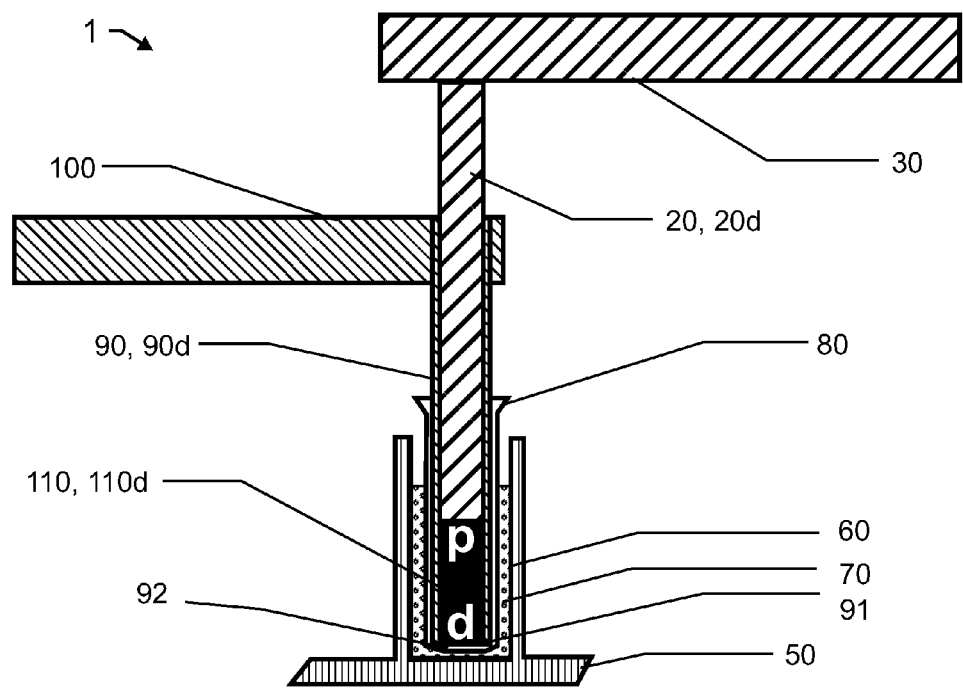
FIG. 3 shows a rod assembly.

FIG. 3 shows a rod assembly 1 according to the present disclosure. The rod assembly 1 comprises a rod element 20 which is fixed to a rod element mechanism. The rod element mechanism in FIG. 3 is a rod element cross beam 30. At a distal end of the rod element 20 is arranged a magnet element 110. The magnet element 110 includes a first magnetic pole at a distal end d, for example, the south pole. In a proximal end p is a second magnetic pole, for example the north pole. A longitudinal axis of the rod element 20 and a longitudinal axis of the magnetic element 110 are substantially coaxially arranged to each other.

The rod element 20 can be in the form of cylindrical tube. Furthermore a form of a thin-walled cylindrical tube or a rod is also possible. Furthermore it is possible to replace the rod element 20 by a wire element or a cord (not shown) wherein the magnet element 110 is fixed at a distal end section of the wire element or cord. A movement of the rod element cross beam 30 in a z-direction is transferred to the rod element 20 and consequently to the magnet element 110. The rod element cross beam 30 therefore enables a movement of the magnet element 110 substantially along a longitudinal axis of the magnet element 110.

The magnet element 110 is located inside a guide element 90. The guide element 90 as shown in FIG. 3 comprises a thin-walled cylindrical tube. Angular embodiments are also possible. The use of the thin-walled cylindrical tube for the guiding element 90 is advantageous, in order to make the magnetic field provided by the magnet element 110 available with little weakening at the exterior surface of the sheath 80. The guide element 90 and the rod element 20 are movable towards one another. The movement of the rod element 20 can be independent of a movement of the guide element 90. The rod element 20 can be drawn by means of the rod element cross beam 30 upwards, while the guide element 90 remains in the cavity 50. Likewise the movement of the rod element 20 and the guide element 90 can take place at the same time. It is desirable to have play of the rod element 20 and the magnet element 110 inside the guide element 90. The play of the rod element 20 and the magnet element 110 inside the guide element 90 prevents the rod element 20 or the magnet element 110 tilting. The play thus ensures a mobility of the rod element 20 and the magnet element 110 in the guide element 90.

The guide element 90 is fixed to a guide element mechanism. The guide element mechanism includes for example a guide element cross beam 100. A movement of the guide element cross beam 100 is passed to the guide element 90, as is the sheath 80 seals a distal end section of the guide element 90. By providing the guide element 90, it is no longer necessary that the sheath 80 is sufficiently inherently stable to enclose the magnet element 110. It is sufficient that a removable connection is made between the sheath 80 and the guiding element 90 to prevent the solution 60 coming into contact with the magnet element 110.

Furthermore due to the presence of the guide element 90, to a large extent an exact positioning of the sheath 80 in the cavity 50 is possible. To a large extent the exact positioning of the sheath 80 prevents a stripping of the magnetizable particles 70 from the sheath 80 by a contact with a wall of the cavity 50.

In contrast to the prior art, the rod assembly 1 enables the magnet element 110 to move through an opening 91 beyond a distal end of the guide element 90 to a distal exposed magnet element position 110$d$*, as shown in FIG. 3. The magnet element 110 can be advanced furthermore near to the sheath 80. It is also of interest that the magnet element 110 is moved beyond the opening 91 of the guide element 90 when the sheath 80 is taken up. It can thus be avoided that the edges of the guide element 90 damage the sheath 80.

In FIG. 3 the magnet element 110 in the distal magnet element position 110$d$ is shown. The distal magnet element position 110$d$ is located at a distal end section of the guide element 90. The distal magnet element position 110$d$ causes the solution 60 to be interspersed with an inhomogeneous magnetic field of the magnet element 110; so there is a force on the magnetizable particles 70 in the solution 60. In other words, the distal end section of the guide element 90 is connected magnetically when the magnet element 110 is located in the distal magnet element position 110$d$.

The magnet element 110 shown in FIG. 3 is shown in the distal magnet element position 110$d$. The distal magnet element position 110$d$ is in a distal end section of the guiding element 90. By the magnet element 110 in the distal magnet element position 110$d$ the distal end section of the guide element 90 is interspersed with the inhomogeneous magnetic field of the magnet element 110. It is to be noted that the distal magnet element position 110$d$ is only defined regarding the distal end section of the guide element 90. In other words, once the magnet element 110 is located in the distal magnet element position 110$d$, the distal end section of the guide element 90 is magnetized and the magnetic field is then enabled. The guide element 90 is shown in FIG. 3 in a distal guide element position 90$d$. The distal guide element position 90$d$ means that the distal end section of the guide element 90 is at least partially immersed in the solution 60 with the magnetizable particles 70, which is located within the cavity 50.

Figure 8:
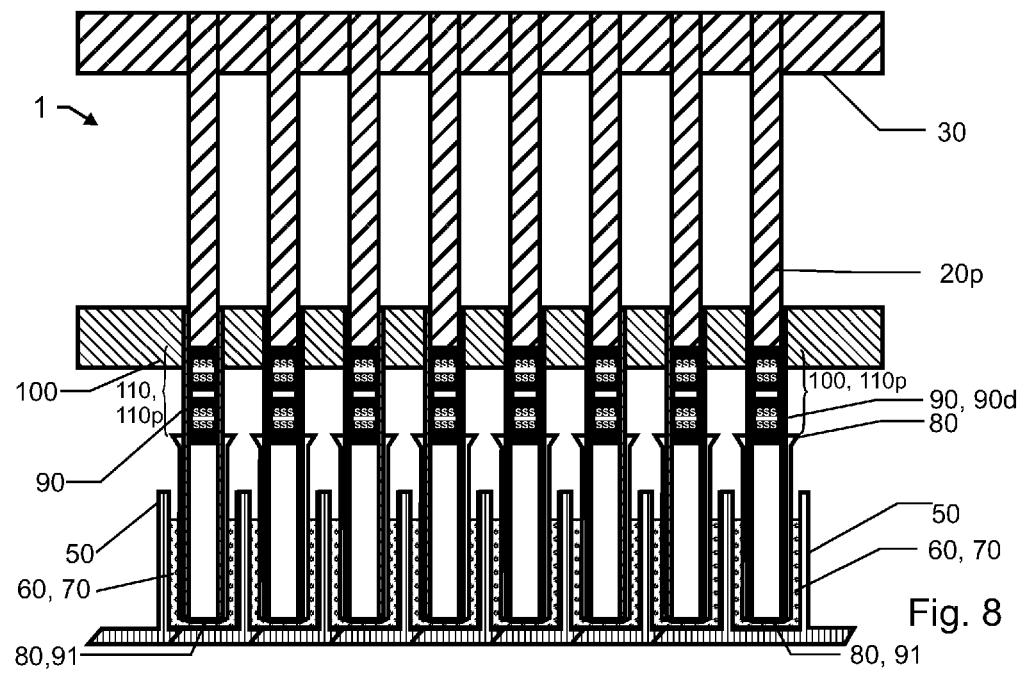
FIG. 8 shows a guide element in a distal guide element position a magnet element in a proximal magnet element position.

The distal magnet element position 110$d$ corresponds to a distal rod element position 20$d$ as shown in FIG. 3. From the distal rod element position 20$d$ the rod element 20 can be moved in a proximal direction to a proximal rod element position 20$p$, as shown in FIG. 8. From the distal rod element position 20$d$ follows for the magnet element 110$a$ proximal magnet element position 110$p$ follows, as for example shown in FIG. 8. The distal magnet element position 110d is clearly shown in FIG. 3. In the distal magnet element position 110d the distal end section of the guiding element 90 is interspersed with the magnetic field of the magnet element 110. This results in a variety of positions for the magnet element 110, which correspond to the proximal magnet element position 110p. Consequently there also exists a variety of proximal magnet element positions 110p for the rod element 20, for example as shown in FIG. 8.

The magnet element 110 in the distal exposed magnet element position 110d* helps to avoid damaging the casing 80 through the edges of the guide element 90 at the distal opening 91 of the guide element 110. Thus thinner and less inherently stable sheaths 80 can be used in comparison to the state of the art. At the same time the manufacturing costs for the sheath 80 is reduced, since the dimensions need no longer fulfill the narrow tolerance requirements.

It is possible to increase by a movement of the magnet element 110 into the distal exposed magnet element position 110d* the magnetizing force of the inhomogeneous magnetic field to extensive surfaces of the sheath 80. Is of course thereby provided that by the movement of the magnet element 110 into the distal exposed magnet element position 110d* of the magnet element 110 the sheath 80 is not damaged. The described movement of the magnet element 110 may therefore take place only within the elastic limits of the sheath 80. The rod assembly 1 in FIG. 3 shows only an individual rod element 20. It is of course possible that the rod assembly 1 comprises a plurality of guide elements 90, a plurality of rod elements 20 and a plurality of magnet elements 110.

Figure 4:
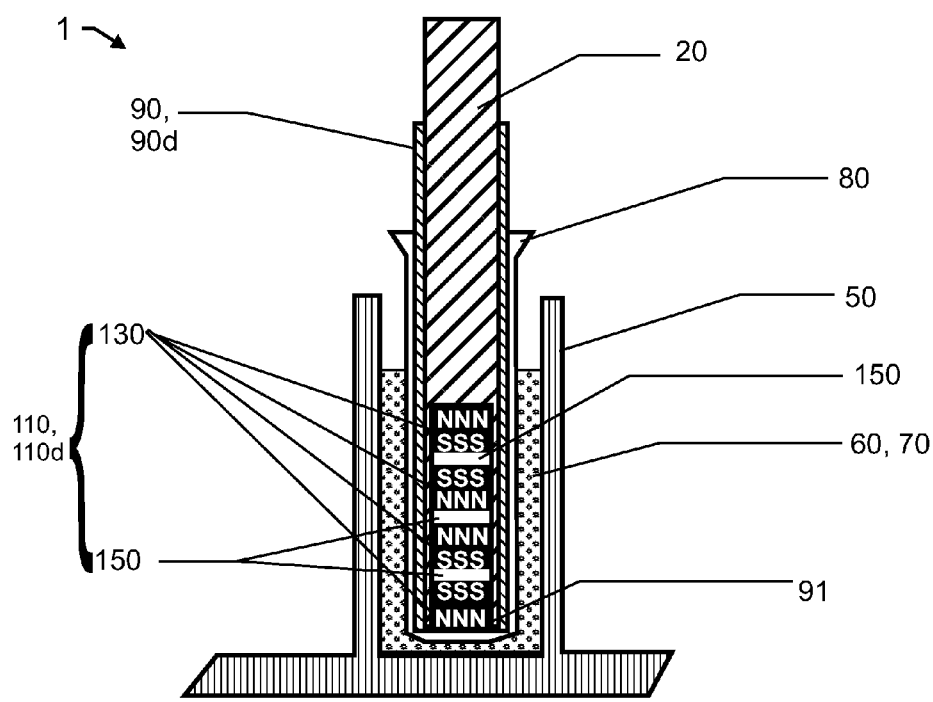
FIG. 4 shows a detail of the rod assembly of FIG. 3.

FIG. 4 shows the guide element 90 in the distal guide element position 90d as well as the magnet element 110 in the distal magnet element position 110d. Elements of FIG. 4 are given the same reference numerals as before. FIG. 4 shows details of the magnet element 110 according to the present disclosure. The magnet element 110 can comprise a plurality of magnetic rods 130. In FIG. 4 are shown four magnetic rods 130. It is of interest that an arrangement of the number of magnetic rods 130 is such that like poles of the magnetic rods 130 are facing each other. Furthermore, the magnet element 110 optionally includes an optional number of spacer elements 150 between each of the magnetic rods 130. The arrangement of like poles facing each other for the bar magnets 130 in conjunction with the spacer element 150 is of interest in order to increase the magnetically active area on the sheath 80, as is discussed below. Instead of a magnetic rod 130 different magnets 130 are possible. The magnetic rods 130 as shown in FIG. 4 are to be understood only as exemplary embodiments. It is of interest to attain as high as possible magnetizing forces of the magnets 130. The magnets 130 should therefore carry a high specific magnetic moment. A possible embodiment of the magnets 130 thus includes, for example, rare earth materials. It is known to the person skilled in the art that rare earth materials carry a high specific magnetic moment. With a high specific magnetic moment of the magnet 130 a high inhomogeneous field strength the extensive areas of the guide element 90 and the extensive areas of the sheath 80 is achieved. Consequently, an adhesion of the magnetizable particles 70 to the circumferential surfaces of the sheath 80 is facilitated. The sheath 80 is resized to fit the dimensions of the guide element 90. An inner diameter of the sheath 80 is adapted to an outer diameter of the guide element 90. The guide element 90 forms a removable connection with the sheath 80. This removable connection can be achieved without limitation by a form fit, a frictional engagement or a clamping clasp K.

Figure 4A:
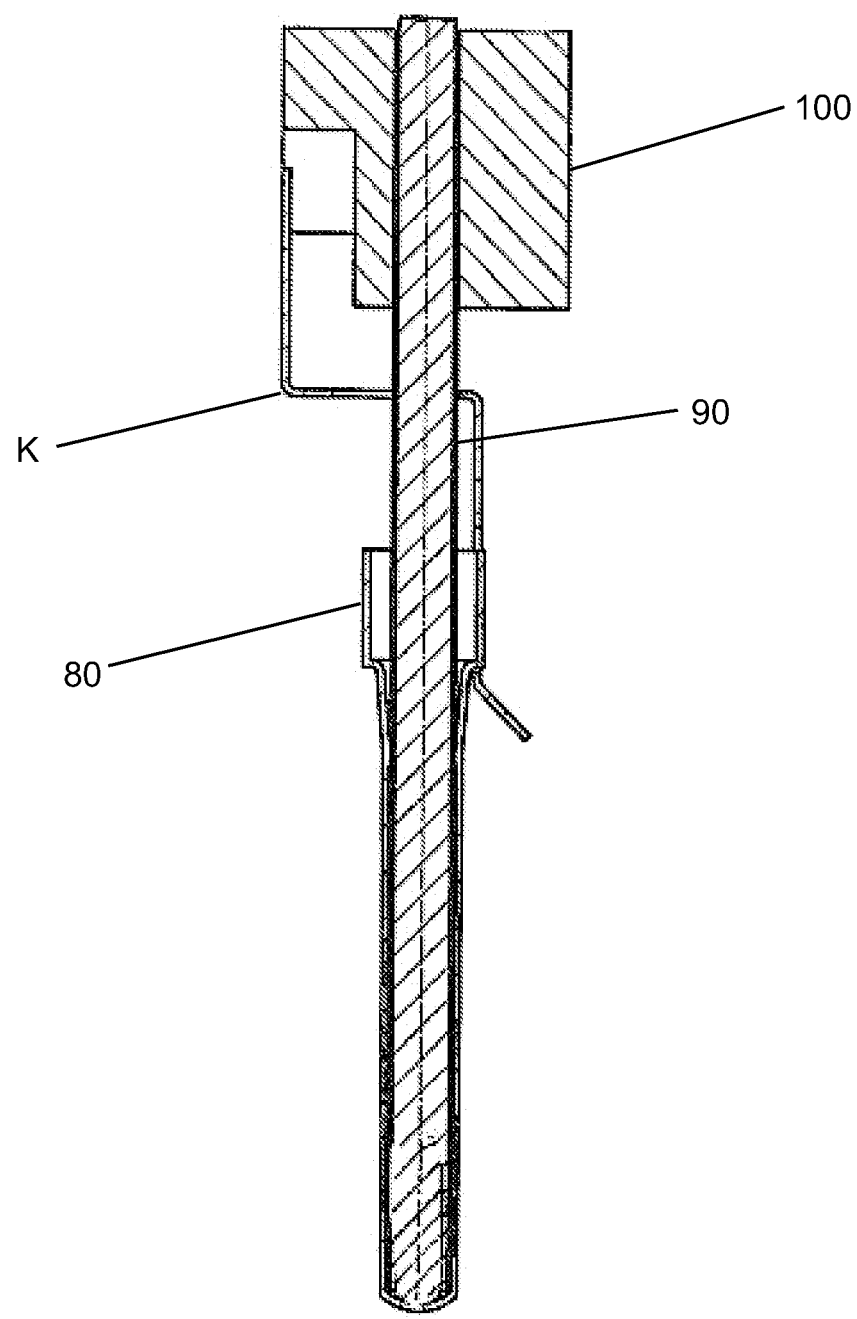
FIG. 4a shows a clamp arrangement.

FIG. 4a shows an example of a clamping clasp K for the removable connection of the guide element 90 with the sheath 80. The clamping clasp K as shown in FIG. 4a is known to the person skilled in the art and shall be described no further.

The spacer element 150 as shown in FIG. 4 comprises substantially a non-magnetic material, for example plastic. Likewise soft magnetic materials are also possible for the spacer element 150. Due to the spacer elements 150 a gap is formed in the field distribution. The field distribution is discussed in detail with reference to FIG. 5. Due to the opposite poles of the magnets 130, there is a repulsive force effect of the individual magnet 130 in an axial direction, in FIG. 4, i.e. repulsion along the perpendicular direction. It is therefore necessary to force the individual magnets 130 in the arrangement as shown in FIG. 4. This can take place via firmly mechanically setting the rod element 20. Alternatively or additionally, the individual magnets 130 can be bonded. The magnets 130 can be realized for example as a short magnetic rod. In short magnetic rods it is to be understand that a length to diameter ratio is less than or equal to 1. Thus, the length-diameter ratio can be for example 4:5. Of course, other possible lengths to diameter ratios are possible. It is possible to manufacture the magnet element 110 as an integral element.

Figure 5:
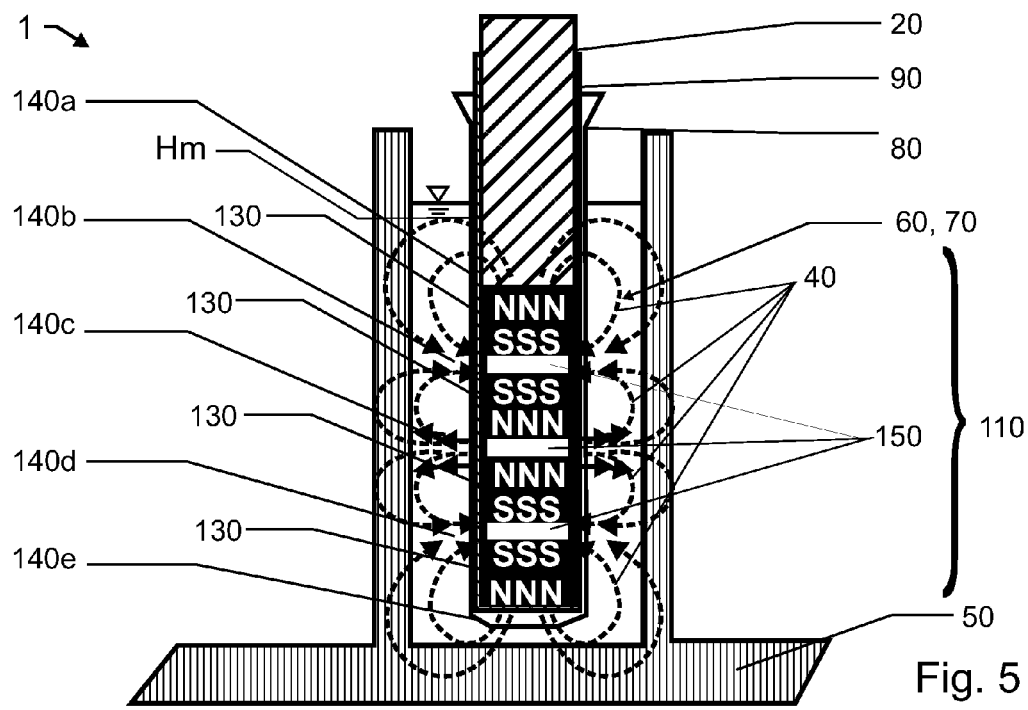
FIG. 5 shows a magnetic field line distribution of a magnet element.

FIG. 5 shows the magnet element 110 from FIG. 4 and additionally the lines of flux and the magnetic field line distribution 40. In FIG. 5 it is shown that that the magnetic field lines, particularly in the areas of the spacer elements 150, are particularly inhomogeneous. Consequently in the area of the spacer elements 150, an increase in an accumulation of the magnetizable particles 70 from the solution 60 results. The area of increased inhomogeneity of the magnetic field is represented in the figure as the areas 140b, 140c and 140d. The area 140a is located above the upper magnet 130, and is thus most proximal to the magnet element 110 as shown in FIG. 5.

The area 140a has no magnets 130 with opposed polarity in the proximal direction. Therefore, there is a less strong inhomogeneous magnetic field distribution than in the areas 140b, 140c and 140d.

The area of increased inhomogeneous magnetizing force 140e is at the distal end of the magnet element 110. For the last magnet 130 that is adjacent to the area 140e, there is missing a magnet 130 with an opposing polarity. The inhomogeneity within the areas 140e is thus not as high, as in the areas 140b, 140c and 140d. By the magnet element 110 as shown in FIG. 5, thus the area of inhomogeneous magnetizing force 140a, 140b, 140c, 140d, 140e can be increased and the size of the magnetically effective surface can be increased. A use of the magnet element 110 as shown in FIG. 5 thus increases a yield of magnetizable particles 70, which deposit themselves within the areas of increased inhomogeneous magnetic field 140a, 140b, 140c, 140d and 140e.

N magnets 130 results in N−1 border areas between the magnets 130, i.e., N−1 ring-shaped sections 140b, 140c, and 140d. The magnetic field lines in these areas, 140b, 140c, and 140d are substantially radial. Due to the radial distribution of the magnetic fields within the areas 140b, 140c, 140d a volume of the cavity 50 is penetrated. The lines of flux are drawn pointing from the north pole to the south pole, whereby the direction of the heads of the arrow results. At areas of high field density the magnetic field is high. Dimensions of the cavity 50 and the magnetic field line distribution 40 can be arranged to each other so that the field lines are limited substantially to the volume of the cavity 50. The available magnetic field is used for penetrating the volume of the cavity 50.

This, of course, increases the yield of the magnetizable particles 70 that adhere in the areas 140a, 140b, 140c, 140d and 140e.

Figure 6:
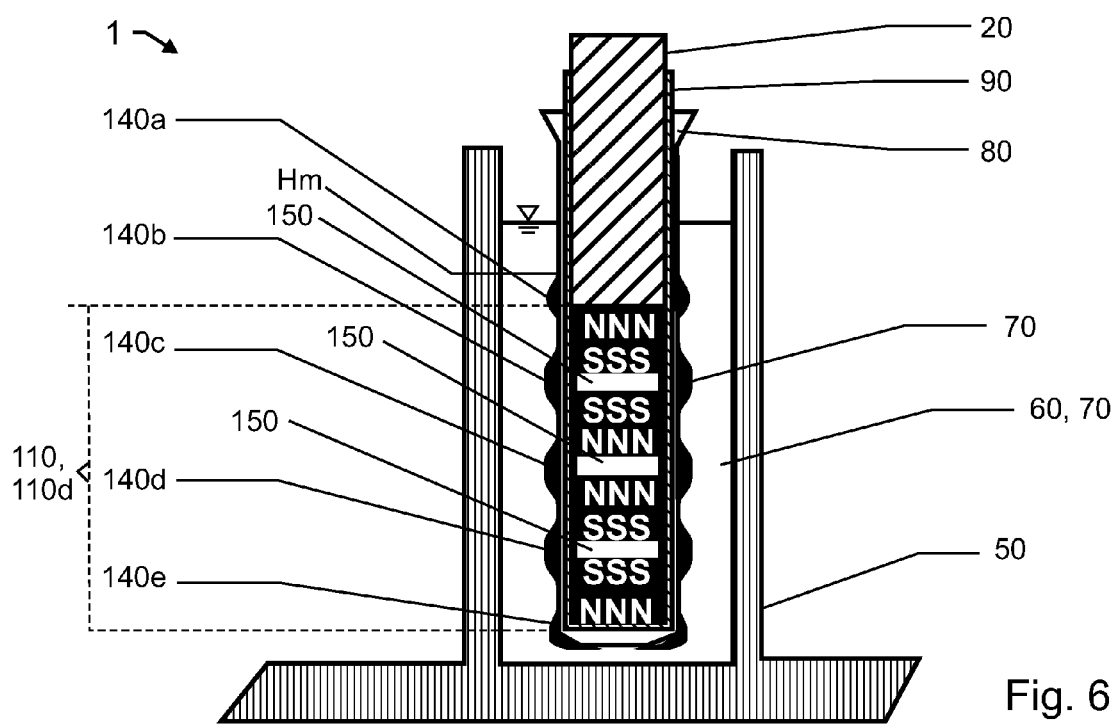
FIG. 6 shows an area, where magnetizable particles settle on the circumferential surface of a guide element, in particular on the circumferential surfaces of a sheath.

It is recommended to provide the sheath 80 with a profile or a radius. In FIG. 6, the sheath 80 is slightly oriented downwardly conical. By such an arrangement of the sheath 80 the inhomogeneous magnetic field available within the area 140e is better utilized. Besides in FIG. 6 the shaping of the sheath 80 as shown helps to avoid a draining-off of the magnetizable particles 70 from the sheath 80.

The magnet element 110 as shown in FIG. 5 can be arranged without restriction and can be arranged transversely to a longitudinal axis of the rod element 20 or the guide element 90. Depending on the dimensions of the guide element 90 and the rod element 20, such an arrangement can be of interest. For the cylindrical embodiment of the rod element 20 and the guide element 90 however a coaxial alignment of the guide element 90 and the magnet element 110 as shown in FIG. 5 may be advantageous, since the magnetic fields provided by the magnet element 110 penetrate the cavity 50 more effectively.

FIG. 6 shows the magnet element 110 according to the present disclosure in the distal magnet element position 110d as already shown in FIG. 5. Instead of magnetic field line distribution 40 is however in FIG. 6 shown, within which areas the magnetizable particles 70 deposit themselves. The accumulation areas correspond to the areas of increased inhomogeneous magnetic field distributions of 140a, 140b, 140c, 140d and 140e. The areas of increased inhomogeneous magnetic field distributions 140a, 140b, 140c, 140d and 140e correspond to the magnetically active areas, as already discussed. It is obvious that with the example shown in FIG. 6 of the magnet element 110, the magnetically active areas increase significantly compared to the prior art, as will be discussed in more detail hereinafter.

According to the example of the magnet element 110 shown in FIG. 6, the magnetized particles 70 annularly deposit at a circumferential surface of the sheath 80 from the solution 60. The proximal ring area 140a is less strongly pronounced than the ring areas 140b, 140c, 140d below.

Figure 7:
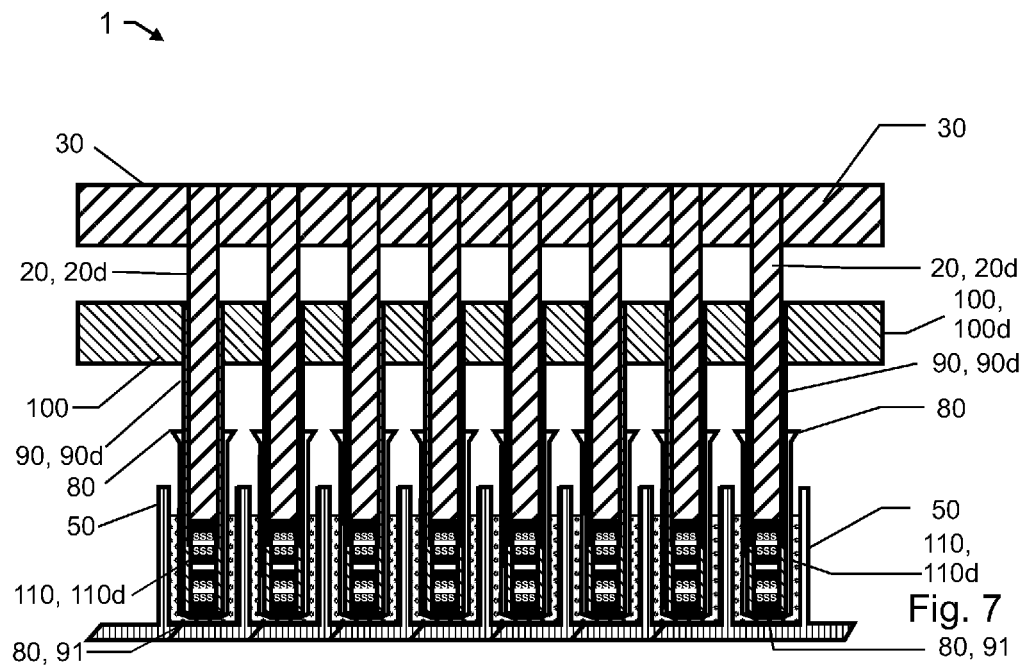
FIG. 7 shows a guide element in a distal guide element position and a magnet element in a distal magnet element position.

In FIG. 7 the magnet element 110 is shown in the distal magnet element position 110d. It is noted that the distal magnet element position 110d is in a distal end section of the guide element 90. The magnet element 110 corresponds to the magnet element 110 shown, for example, in FIG. 6. For better clarity, however, only the south poles of the individual magnets 130 are shown. By immersing the magnet element 110 into the solution 60, the guide element 90 is moved to the distal guide element position 90d, for example, by use of the guide element cross beam 100. For the magnet element 110 to remain during this movement of the guide element 90d in the distal magnet element position 110d the rod element 20 has to be moved from a proximal rod element position 20p to a distal rod element position 20d, as shown in FIG. 7. For the movement of the rod element 20 the rod element the cross beam 30 can be used. FIG. 7 shows eight guiding elements 90 and eight rod elements 20 for exemplary purposes. All other features of FIG. 7 were already discussed with reference to the previous figures and are given the same reference numerals. It is again noted that the rod element 20 and the guide element 90 are independently movable.

In FIG. 8 the magnet element 110 is shown for example in a proximal magnet element position 110p. By a movement of the magnet element 110 into the proximal magnet element position 110p the distal end section of the guide element 90 is non-magnetically switched. The guide element 90 held in the cavity 50 stabilizes a position of the sheath 80. In addition the guide element cross beam 100 remains in a position, such that the guide elements 90 remains in the distal guide element position 90d. A movement of the rod element cross beam 30 can be made by drive means as well as a movement of the guide element cross beam 100 by suitable drive means, as will be explained below.

FIG. 9 shows the guide element 90 in the proximal guide element position 90p with the distal end section of the guide elements 90 remaining magnetized. The magnetization of the distal end section of the guide elements 90 is achieved by retention of the magnet element 110 in the distal magnet element position 110d. It will be recalled that the distal magnet element position 110d is determined by a positioning of the magnet element 110 within a distal end section of the guide element 90. In order to reach a position of the guide element 90 as in FIG. 9 with the magnet element 110 in the distal magnet element position 110d, a movement in a z-direction of the rod element cross beam 30 and the guide element cross beam 100 must be coordinated. Such coordination can take place, for example, via suitable control software. In the position shown in FIG. 9 of the guide elements 90 and the rod elements 20, the guide elements 90 are in a proximal guide element position 90p and the rod elements 20 are in a proximal rod element position 20p. It is noted that a plurality of proximal rod element positions 20p exists for a rod element 20. It is noted that a plurality of proximal guide element position 90p exists for the guide element 90. The position shown in FIG. 9 of the guide elements 90 and the bar elements 20, and thus the magnet elements 110 in the distal magnet element position, allows a transportation of the sheath 80 with deposited magnetizable particles 70. The transportation may include a lifting of the magnetizable particles 70 from the solution 60. The magnetizable particles 70 adhered to the sheath 80 can also be transported from a first cavity 50 into a second cavity. So it is for example possible, to gather further magnetizable particles 70 from a further solution 60 in addition to the magnetizable particles 70 already adhered to circumferential surfaces of the sheath 80.

FIG. 10 shows a comparison of the magnet element 110 according to an aspect of the disclosure with a single bar magnet as the magnet element 110. FIG. 10 (left) shows the magnet element 110 in the distal magnet element position 110d. The magnet element 110 comprises, for example, four short magnetic rods 130 as well as the spacer elements 150. In addition the magnetic field line distribution 40 is shown. The areas of increased inhomogeneous magnetic field distributions 140b, 140c and 140d are also shown. To the right of FIG. 10 is shown for comparison, the magnet element 110 in the distal magnet element position 110d. In contrast to the left hand side, the right hand side of the image in FIG. 10 includes a single magnet 130, which is for example a long magnet rod. The field distribution for the individual magnet rod 130 is less inhomogeneous than for the magnet element 110 of the present disclosure. In addition, the magnetic field lines of the magnetic field line distribution 40 as shown in the right hand side of the figure picture are shown to clearly penetrate further into a volume of the cavity 50. Therefore the available magnetizing force of the magnet element 110 is less effective for gathering magnetizable particles 70 from the solution 60.

The right hand side of FIG. 10 shows that there remains only a small area of increased inhomogeneous magnetic field line distribution 140. The surface of increased the inhomogeneous field line distribution is clearly smaller for the individual magnet 130. The comparison in FIG. 10 clearly shows that the magnetically active surfaces using the magnet element 110 according to the present disclosure increases significantly compared with the single bar magnet, as is known in the prior art.

It is possible in any case, to combine the magnet element 110 according to the present disclosure with known rod arrangements for extracting the magnetizable particles 70. This would increase the effectiveness of the already known rod assemblies. Therefore the present disclosure comprises the magnet element 110 as such.

Figure 11:
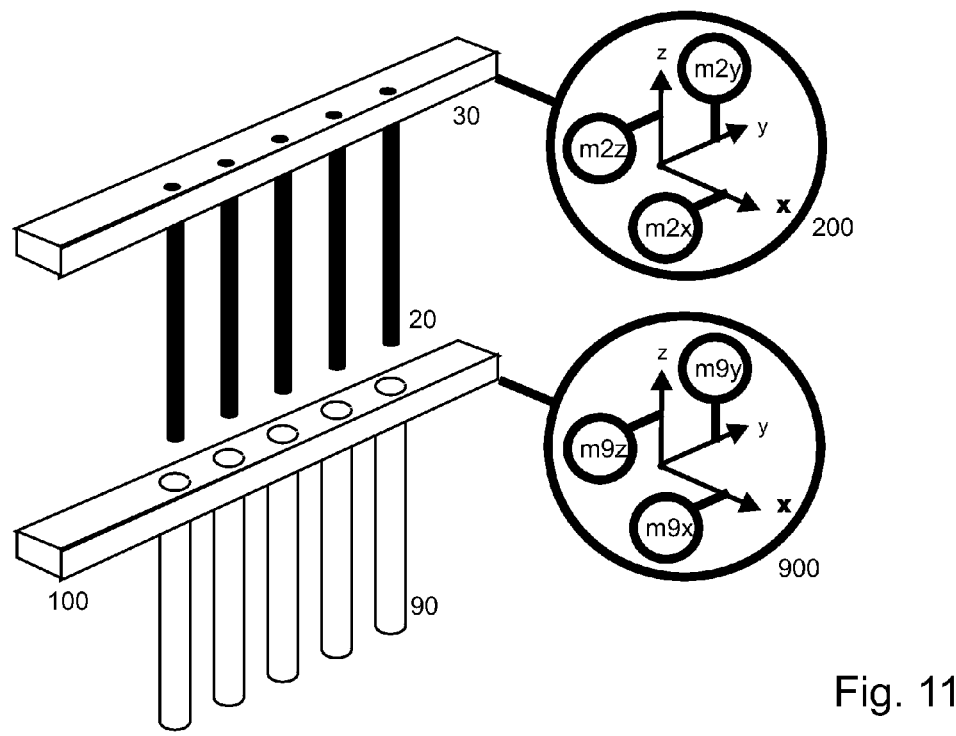
FIG. 11 shows various drive means for moving a magnet element and a guide element.

The rod assembly 1 in accordance with the present disclosure can comprise drive means. As shown in FIG. 11, the rod element cross beam 30 with the rod element 20 is movable by a group of rod element drive means 200. The group of rod element drive means 200 can comprise up to three actuators acting orthogonally: a first rod element drive means m2x for a movement in an x-direction; a second rod element drive means m2y for a movement in a y-direction and a third rod element drive means m2z for a movement in a z-direction. The three rod element drive means m2x, m2y and m2z are independently moveable. The guide element cross beam 100 can be moved by means of a group of guide element drive means 900, whereby a movement of the guide element 90 results. The group of guide element drive means 900 can comprise up to three independent and separately controllable drive means: a first guide element drive means m9x for moving the guide element cross beam 100 in a in x-direction. A second guide element drive means m9y for moving the guide element cross beam 100 in a y-direction. A third guide element drive means m9z for moving the guide element cross beam 100 in a z-direction. The group of rod element drive means 200 and the group of guide element drive means 900 are individually controllable. It may be provided a special control system for controlling and regulating the two element drive means 200 and 900, as would be well known to the person skilled in the art.

Figure 12:
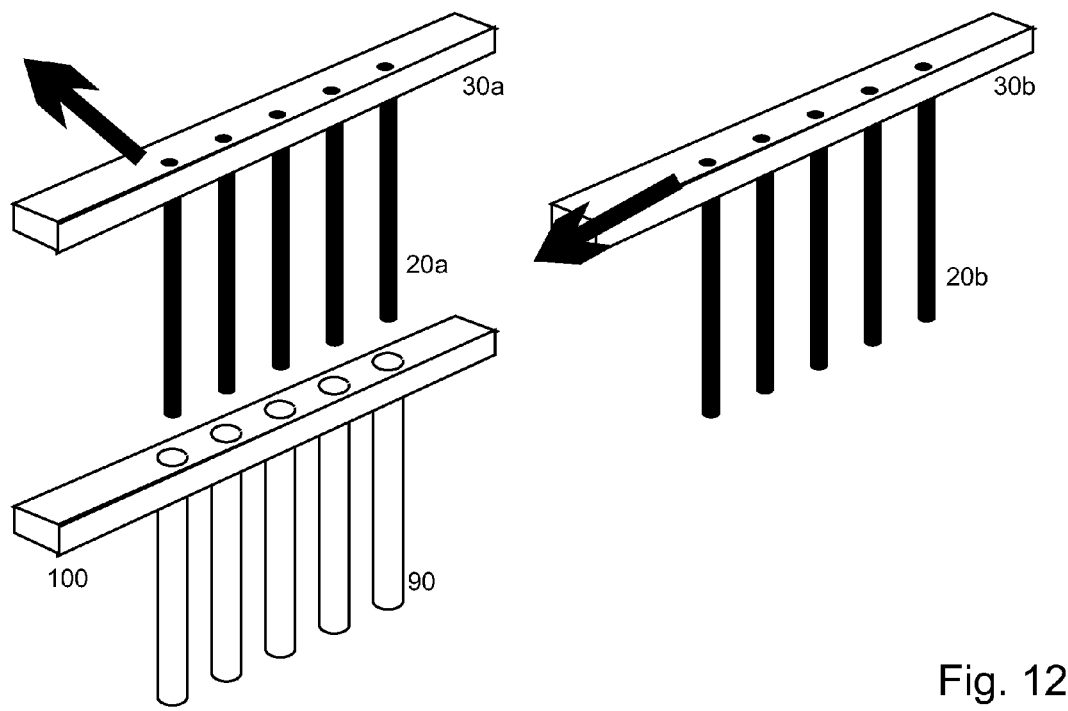
FIG. 12 shows a magnet element in a position for changing the magnet elements.

FIG. 12 shows how changing of the rod elements 20 and thus the magnet elements 110 (not shown) is possible. The group of rod element drive means 200 for moving the rod element cross beam 30 allows a movement of a first rod element cross beam 30a in the proximal direction, away from the guide element cross beam 100. Therefore it is possible that that a first rod element 20a of a first rod element cross beam 30a are removed completely out of the guide element 90 of the guide element cross beam 100 as shown in FIG. 12 above left. As soon as the first rod elements 20a, which are connected with the first rod element cross beam 30a, is removed completely out of the guide element 90, a second group of rod elements 20b can be introduced into the guide element 90 of the guide element cross beam 100, by means of a second rod element cross beam 30b. The group of first rod element drive means 200 enables the required movement of the rod elements 20 for a changing of the rod elements 20. Changing the magnet elements 110 through an exchange of the rod elements 20 is beneficial to ensure that all areas 140 for the deposition of the magnetizable particles 70 are always covered with the solution 60. More generally changing of the magnet elements 110 allows the adjustment of the magnetic fields of the magnetic elements 110 to the dimensions of the cavity 50 and/or a filling height of the solution 60 within the cavity 50.

For the skilled person it is also obvious that the group of element drive means 200, 900, allows a circular movement of the rod elements 20 and the guide element 90 in a plane. Thus a circular mixing motion within the cavities 50 is possible.

A change of the rod elements 20 can be, for example, of interest, in order to allow different strengths of magnetization affect on the solution 60 within the cavities 50. It is preferable to connect the guide element 90 firmly with the guide element cross beam 100. As previously mentioned, it is of interest that the attachment of the rod element 20 to the rod element cross beam 30 has a slight play. A certain play of the rod elements 20 to the rod element cross bean 30 allows a guidance of the rod element 20 by the guide element 90, whereby a tilting of the rod element 20 in the guide element 90 is avoided. Strictly speaking, a mechanical over determination is avoided by the guide element 90 and the rod element 20.

Figure 13:
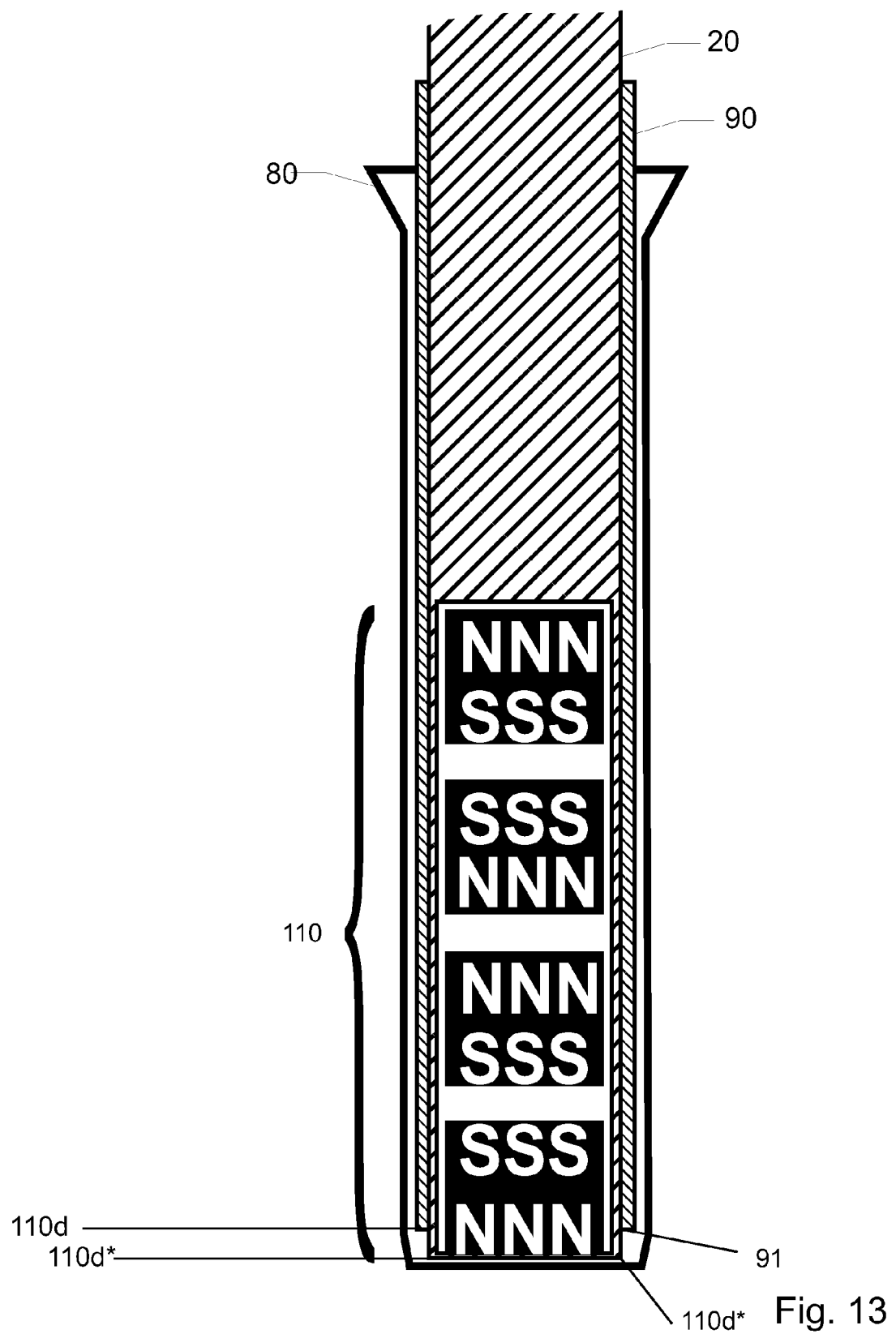
FIG. 13 shows a magnet element in a distal exposed magnet element position.

FIG. 13 shows a guide element 90 with an opening 91 of the guide element 90 at a distal end section of the guide element 90. Inserted into the guide element 90 is a rod element 20, which carries at a distal end portion a magnet element 110. For the rod assembly 1, it is possible that the magnet element 110 is moveable over a distal magnet element position 110d in a distal direction, at least in part, through the opening 91 of the guide element 90. In FIG. 13, the magnet element 110 is shown in the distal exposed magnet element position 110d*. In the distal exposed magnetic element position 110d* the magnetic element 110 extends over a distal end of the guide element 90. Due to the distal exposed magnet element position 110d*, the magnet element 110 can be moved closer to the sheath 80. With the magnet element 110 in the distal exposed magnet element position 110d* sliding of the sheath 80 on the guide device 90, as already described, is facilitated. When the magnet element 110 is in the distal exposed magnet element position 110d* then damage of the sheath 80 is avoided while sliding up the sheath 80. A damage of the sheath 80 is to be feared in particular if the sheath 80 has no sufficient inherent stability. With sufficient elasticity of the sheath 80 the magnet element 110 can move into the distal exposed magnet element position 110d*, without the sheath 80 being damaged. The magnet element 110 in the distal exposed magnet element position 110d* is increased beyond the inhomogeneous magnetic field, which the solution 60 and thus the magnetizable particles are exposed to 70. The force on the magnetizable particles 70 will be increased by means of the distal exposed magnet element position 110d*.

The disclosure further describes a method 500 for the extraction of magnetizable particles 70 from the solution 60 in at least one cavity 50.

Figure 14:
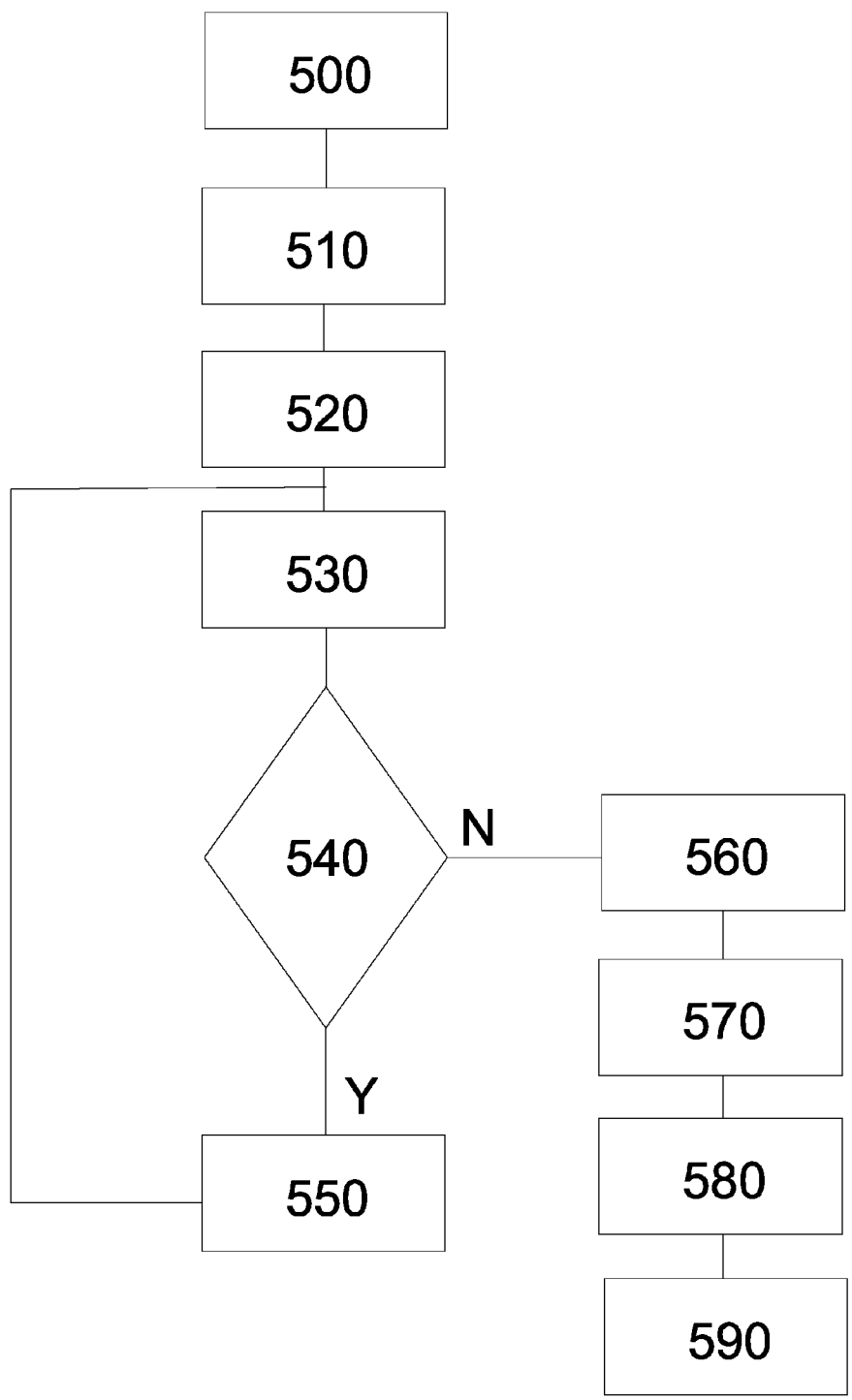
FIG. 14 shows a flow chart of a method.

FIG. 14 shows the steps of the method 500. A step 510 comprises a taking up of the sheath 80 to at least one of the guide elements 90 and/or a closure of the opening 91 at the distal end of the at least one guide element 90 by a sealing element 92. The closing of the opening 91 can replace a taking up of the sheath 80 or can additionally comprise taking up the sheath 80 in the step 510. The step 510 of taking up the sheath 80 can comprise for example a frictional engagement between the sheath 80 and the guide element 90. In addition, for receiving the sheath 80, the magnet element 110 can be moved to the distal exposed magnet element position 110d*, as shown in FIG. 13. In addition to taking up the sheath 80, a use of a clamping clasp K, as shown in FIG. 4a, is possible. The person skilled in the art is aware of further possibilities for taking-up of the sheath 80 on the guide element 90, which are not discussed further.

In a step 520 is a mixing of the solution 60. The mixing of the solution 60 in step 520 is used to mix the magnetizable particles 70 that are located within the solution 60. It is to be prevented by the mixing that any magnetizable particles 70 are not only located in a bottom area of the cavity. Mixing the solution 60 is followed by a step 530 for collecting the magnetizable particles 70 from the solution 60. In step 530 the collecting the magnetizable particles 70, thus an extraction of magnetizable particles 70 and consequently bound biomolecules with the magnetizable particles 70 from the solution 60 is possible.

In a step 540 a determination is made whether the magnetizable particles 70 and/or the magnetizable particle-biomolecules complexes that have already been collected, are to be transported to another cavity 50. If necessary, transporting 550 of the magnetizable particles 70 to the further cavity 50 occurs. If no further solution 60 is intended, then transporting 560 to a goal cavity takes place. The goal cavity can comprise for example a result container, in which the magnetizable particles 70 are concentrated. After the concentration, a separation of the biomolecules from the magnetizable particles 70 can occur. A separation of the magnetizable particles 70 of the biomolecules takes place then in a further step. Transporting 560 to the goal cavity is possible by means of the group of element drive means 200, 900, which permit the movement of the guide element 100 and the rod element cross beam 30. If a further solution 60 is desired, following the step 540 transporting 550 to the further solution 60 is implemented. Transporting 550 to the further solution 60 can take place via the means of the group of element drive means 200, 900. After the step 550 for transport to the further solution 60 the process returns back to step 530 for collecting the magnetizable particles 70. The transport of the magnetizable particles 70 to the goal cavity 50 includes a step 570 for detaching the magnetizable particles 70 from the sheath 80. The detachment 570 can be influenced by a mixing, as described in step 520. The separation 570 of the magnetizable particles 70 from the sheath 80 can comprise also a separation of the magnetizable particles 70 of the biomolecules, which were bound to the magnetizable particle 70 under formation of the particle biomolecule complex. For the separation of the biomolecules from the magnetizable particles 70, elution solutions and elution procedures are known. These elution procedures are not part of the disclosure, but well known to the person skilled in the art. Therefore the separation of the biomolecules from the magnetizable particles 70 using the elution procedures is discussed no further. In a step 580, the guide elements 90 are lifted from the cavity 50. A step 590 can follow for the separation of the sheath 80 from the guide element 90.

Figure 15:
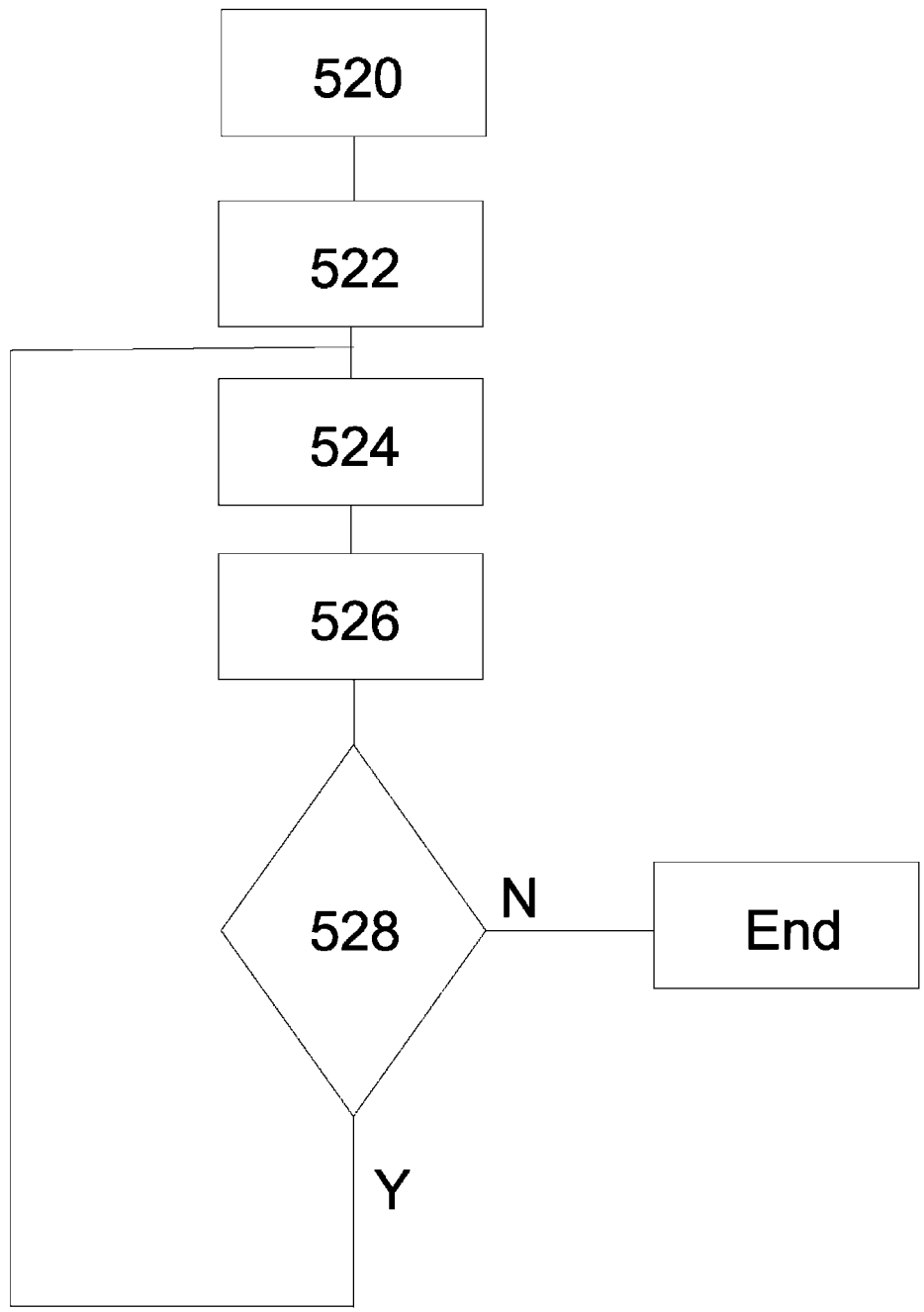
FIG. 15 shows details of a step for mixing a solution.

FIG. 15 shows details of the step 520 for mixing the solution 60. A step 522 comprises a moving of the magnetizable element 110 into a proximal magnet element position 110p. The proximal magnetic element position 110p means that the distal end of the guide element 90 is no longer traversing the magnetic field of the magnet element 110. In a step 524, the guide element 90 is moved in the distal guide element position 90d. Typically in this step the guide element 90 immerses into the solution 60 in the cavity 50. Subsequently, the guide element 90 in a step 526 is moved into the proximal guide element position 90p. In other words in the steps 522 to 526 the un-magnetized guide element 90 is immersed into the solution 60 and then lifted from the solution 60. In a step 528 it is determined whether further mixing is necessary. If no further mixing is necessary, the step 520 is terminated. If further mixing is necessary, the method returns to the step 524.

Figure 16:
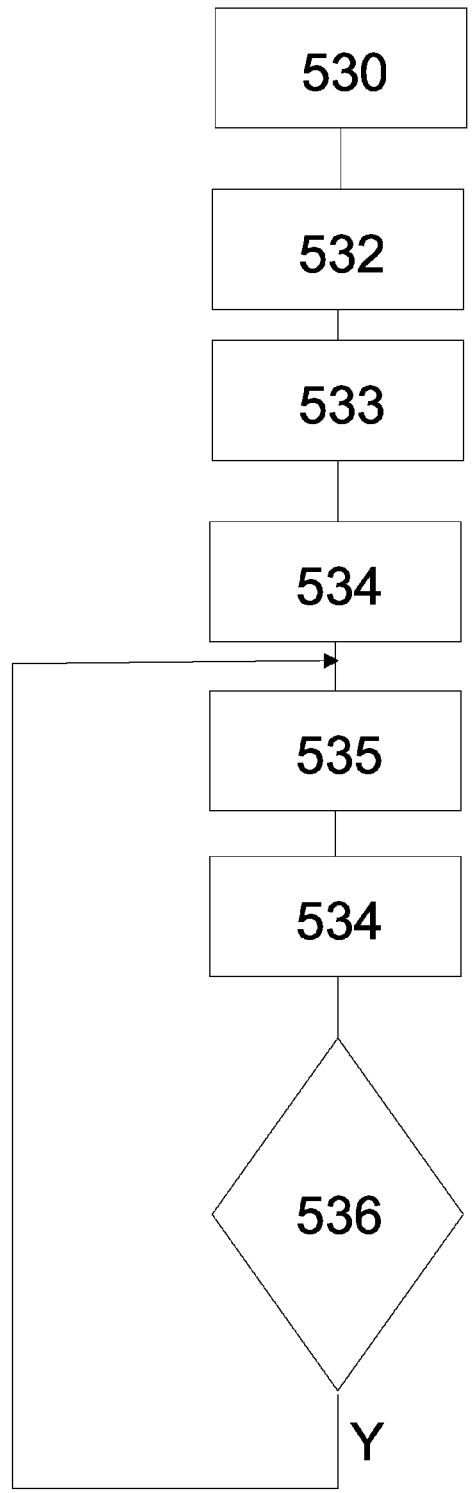
FIG. 16 shows details of a step for collecting the magnetizable particles.

FIG. 16 shows details of the step 530 for gathering the magnetizable particles 70. A step 532 comprises moving the guide element 90 into the distal guide element position 90d. This is followed in a step 533 by a movement of the magnet element 110 in the distal magnet element position 110d, if the magnetic element 110 is not already located in the distal magnetic element position 110d. In the step 533 a moving of the magnet element 110 in the distal magnetic element position 110d may also include a displacement of the magnet element 110 in the distally exposed position of magnetic element 110d*, as shown in FIG. 13.

In a step 534 a movement of the guide element 90 in the proximal guide element position 90p occurs. The magnet element 110 remains in step 534 in the distal magnetic element position 110d or the distal exposed magnet element position 110d*.

In a step 535, the guide element 90 is moved in the distal guide element position 90d, wherein the magnet element 110 in the distal magnet element position 110d or the distal exposed magnet element position 110d* remains. That is, the distal end section of the guide element 90 remains magnetized.

The step 534 is repeated for moving the guide elements 90 in the proximal position.

In step 536 it is determined if a further collection step 530 is required. If a further step 530 is required for collection, the method returns back to the step 535.

The features and aspects of various embodiments of the invention are identified in the description and drawings hereof, with reference numerals tabulated below.

Reference Numerals

1 Rod assembly
20 Rod element
20d Distal rod element position
20p Proximal rod element position
30 Rod element cross beam
40 Magnetic field line distribution
50 Cavity
60 Solution
70 Magnetizable particles
80 Sheath
90 Guide element
90d Distal guide element position
90p Proximal guide element position
91 Opening
92 Closable element
95 Proximal opening
100 Guide element cross beam
110 Magnet element
110d Distal magnet element position
110d* Distal exposed magnet element position
110p Proximal magnet element position
130 Magnetic rods
140 Area of increased inhomogeneous magnetic field line distribution
150 Spacer element
200 Group of rod element drive means
500 Method
510 Receiving
520 Mixing
530 Collecting
900 Group of guiding element drive means While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A rod assembly for the extraction of magnetizable particles from solutions in at least one cavity, the rod assembly comprising:
   at least one guide element, moveable to a distal guide element position wherein the at least one element consists essentially of substantially non-magnetic materials;
   at least one rod element, wherein the rod element is insertable in the at least one guide element and is moveable in a direction substantially parallel to the at least one guide element;
   a magnet element arranged on a distal end portion of the at least one rod element, whereby the magnet element is movable to a distal magnet element is position and whereby the distal magnet element position is present on a distal end section of at least one guide element; and wherein the at least one guide element compromises an opening at a distal end.

2. The rod assembly according to claim 1, wherein the magnet element is moveable through the opening at the distal end of the guide element in a distal exposed magnet element position.

3. The rod assembly according to claim 1, wherein the at least one guide element is also moveable between a proximal guide element position and the distal guide element position.

4. The rod assembly according to claim 1, wherein the magnet element is also moveable between a proximal magnet element position and the distal magnet element position.

5. The rod assembly according to claim 1, wherein the at least one rod element relative to the at least one guide element is moveable between a proximal rod position and a distal rod position.

6. The rod assembly according to claim 1, wherein the at least one guide element is independently moveable of the magnet element.

7. The rod assembly according to claim 1, wherein the at least one rod element is independently moveable of the at least one guide element.

8. The rod assembly according to claim 1, wherein the at least one guide element and the magnet element are moveable together along the direction substantially parallel to the at least one guide element.

9. The rod assembly according to claim 1, wherein a mobility of the at least one guide element includes a mobility of the at least one guide element with a disposition of the magnet element in the distal magnet element position.

10. The rod assembly according to claim 1, wherein a mobility of the at least one guide element includes a mobility of the at least one guide element with the disposition of the magnet element in the proximal magnet element position.

11. The rod assembly according to claim 1, wherein the mobility of the at least one guide element comprises a mobility of the magnet element to a distal end and beyond of the at least one guide element so that the magnet element of the at least guide element is spaced apart and the at least one guide element does not follow the movement of the magnet element.

12. The rod assembly according to claim 1, wherein there is fixed to the at least one guide element a guide element mechanism for the movement of the at least one guide element.

13. The rod assembly according to claim 12, wherein the guide element mechanism comprises at least one guide element cross beam.

14. The rod assembly according to claim 13, wherein the at least one guide element cross beam is moveable in at least one direction substantially perpendicular to the at least one guide element.

15. The rod assembly according to claim 13 further comprising a driver for moving the at least one guide element cross beam in a direction substantially parallel to the at least one guide element.

16. The rod assembly according to claim 13 further comprising a driver for moving the at least one guide element cross beam in a direction substantially perpendicular to the at least one guide element.

17. The rod assembly according to claim 1, wherein the at least one guide element comprises a beam-like guide element.

18. The rod assembly according claim 1, wherein the at least one guide element comprises a cylindrical tube.

19. The rod assembly according to claim 18, wherein the cylindrical tube comprises a thin walled cylindrical tube.

20. The rod assembly according to claim 1 further comprising a rod element mechanism connected to the at least one rod element to enable movement of the at least one rod element.

21. The rod assembly according to claim 20, wherein the rod element mechanism allows a movement of the at least one rod element in substantially an axis parallel direction to that at least one guide element.

22. The rod assembly according to claim 20, wherein the rod element mechanism comprises at least one rod element cross beam.

23. The rod assembly according claim 22, wherein the at least one rod element cross beam is moveable in at least one direction substantially perpendicular to the at least one guide element.

24. The rod assembly according to claim 22, further comprising a driver for moving the at least one rod element cross beam in a direction substantially parallel to the at least one guide element.

25. The rod assembly according claim 22, further comprising a driver for moving the at least one rod element cross beam in a direction substantially perdendicular to the at least one guide element.

26. The rod assembly according to claim 1, wherein the at least one rod element comprises substantially non-magnetic material.

27. The rod assembly according to claim 1, wherein the at least one rod element comprises a cylindrical tube.

28. The rod assembly according to claim 27, wherein the cylindrical tube comprises a thin walled cylindrical tube.

29. The rod assembly according to claim 1, wherein the opening at the distal end of the at least one guide element is closable.

30. The rod assembly according to claim 1, wherein the opening at the distal end of the at least one guide element is closable though a closable element.

31. The rod assembly according to claim 30, wherein the closable element comprises of substantially non-magnetic material.

32. The rod assembly according claim 1, wherein the at least one guide element exhibits a proximal opening, wherein the proximal opening is adapted to receiving the at least one rod element.

33. The rod assembly according to claim 1 further comprising a sheath, which is adapted to close the distal end portion of the at least one guide element.

34. The rod assembly according to claim 33, wherein the at least one guide element is removable from the sheath.

35. The rod assembly according to claim 33, wherein a holder connecting the at least one guide element and the sheath is removable.

36. The rod assembly according to claim 1, wherein the magnet element comprises a plurality of magnetic rods.

37. The rod assembly according to claim 36, wherein the plurality of magnetic rods comprise short magnetic rods.

38. The rod assembly according to claim 37, wherein two or more of the plurality of magnetic rods are arranged with regards to each other in a direction substantially parallel to the at least one guide element with repulsive poles.

39. The rod assembly according to claim 37, wherein a length of the magnet element and a liquid quantity are coordinated in at least a cavity such that that during the extraction of the magnetizable particle from the solution a climbing height of the solution is at least the same or larger than the length of the magnet element.

40. The rod assembly according to claim 36, wherein two or more of the plurality of magnetic rods are arranged with regards to each other in a direction substantially parallel to the at least one guide element with repulsive poles.

41. The rod assembly according to claim 36, wherein between each one of the plurality of magnetic rods is located at least one spacer element.

42. The rod assembly according to claim 41, wherein the at least one spacer element comprises of substantially non-magnetic material.

* * * * *